United States Patent
Kuo et al.

(10) Patent No.: US 9,943,239 B2
(45) Date of Patent: Apr. 17, 2018

(54) OPTICAL SENSING SYSTEM AND ASSOCIATED ELECTRONIC DEVICE

(71) Applicant: TAIWAN SEMICONDUCTOR MANUFACTURING COMPANY LTD., Hsinchu (TW)

(72) Inventors: Hung-Yi Kuo, Taipei (TW); Hao-Yi Tsai, Hsinchu (TW); Hsien-Ming Tu, Hsinchu County (TW); Shih-Wei Liang, Taichung County (TW); Chang-Pin Huang, Taoyuan County (TW); Chih-Hua Chen, Hsinchu County (TW); Yu-Feng Chen, Hsinchu (TW); Chen-Hua Yu, Hsinchu (TW)

(73) Assignee: TAIWAN SEMICONDUCTOR MANUFACTURING COMPANY LTD., Hsinchu (TW)

( * ) Notice: Subject to any disclaimer, the term of this patent is extended or adjusted under 35 U.S.C. 154(b) by 0 days.

(21) Appl. No.: 15/062,901

(22) Filed: Mar. 7, 2016

(65) Prior Publication Data

US 2017/0251937 A1    Sep. 7, 2017

(51) Int. Cl.
*A61B 5/024* (2006.01)
*H04B 10/40* (2013.01)
*A61B 5/00* (2006.01)

(52) U.S. Cl.
CPC .......... *A61B 5/02427* (2013.01); *A61B 5/721* (2013.01); *H04B 10/40* (2013.01)

(58) Field of Classification Search
CPC ............ A61B 5/02416; A61B 5/02427; A61B 5/02433; A61B 5/721
See application file for complete search history.

(56) References Cited

U.S. PATENT DOCUMENTS

| | | | |
|---|---|---|---|
| 2013/0200528 A1* | 8/2013 | Lin | H01L 21/6836 257/774 |
| 2014/0275852 A1* | 9/2014 | Hong | A61B 5/02427 600/301 |
| 2015/0109785 A1* | 4/2015 | Kerness | G01J 1/0271 362/253 |
| 2015/0112207 A1* | 4/2015 | Inoue | A61B 5/681 600/479 |
| 2016/0029911 A1* | 2/2016 | Lee | A61B 5/02427 600/301 |
| 2017/0117242 A1* | 4/2017 | Ho | H01L 24/16 |

FOREIGN PATENT DOCUMENTS

WO    WO 2014/178793    * 11/2014

* cited by examiner

*Primary Examiner* — Allen Porter, Jr.
(74) *Attorney, Agent, or Firm* — WPAT, P.C., INTELLECTUAL PROPERTY ATTORNEYS; Anthony King

(57) ABSTRACT

An optical sensing system is disclosed. The optical sensing system includes a printed circuit board (PCB), a supporter and an optical sensor. The PCB includes a top surface, a bottom surface and a through cavity, wherein the through cavity extends downwardly from the top surface to the bottom surface. The supporter has a top surface and a bottom surface. The optical sensor is bonded and coupled to the top surface of the supporter, wherein the optical sensor includes a primary optic structure. Wherein the supporter is flipped over and bonded to the PCB with the top surface facing the through cavity, so that the optical sensor is coupled to the PCB and at least partially extends to the through cavity. Associated electronic devices are also disclosed.

20 Claims, 16 Drawing Sheets

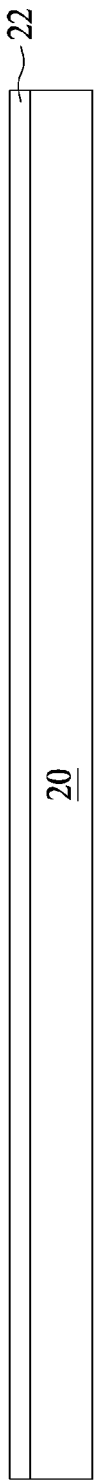

FIG. 9

OPTICAL SENSING SYSTEM AND ASSOCIATED ELECTRONIC DEVICE

BACKGROUND

Photoplethysmography (PPG) is a technology for measuring physiological parameters by shining light at a specific wavelength into the body and measuring the return signal (either through an extremity such as a finger or from reflections of the body). Unfortunately, PPGs are very sensitive to noise and cannot distinguish between the different factors including heart rate, breath rate and body motion, affecting the blood flow.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIGS. 1 through 8 are schematic views illustrating intermediate stages in the manufacturing of an optical sensing system in accordance with some exemplary embodiments of the present disclosure;

FIGS. 9 through 13 are schematic views illustrating intermediate stages in the manufacturing of an optical sensing system in accordance with some exemplary embodiments of the present disclosure.

DETAILED DESCRIPTION

Figure 2A:
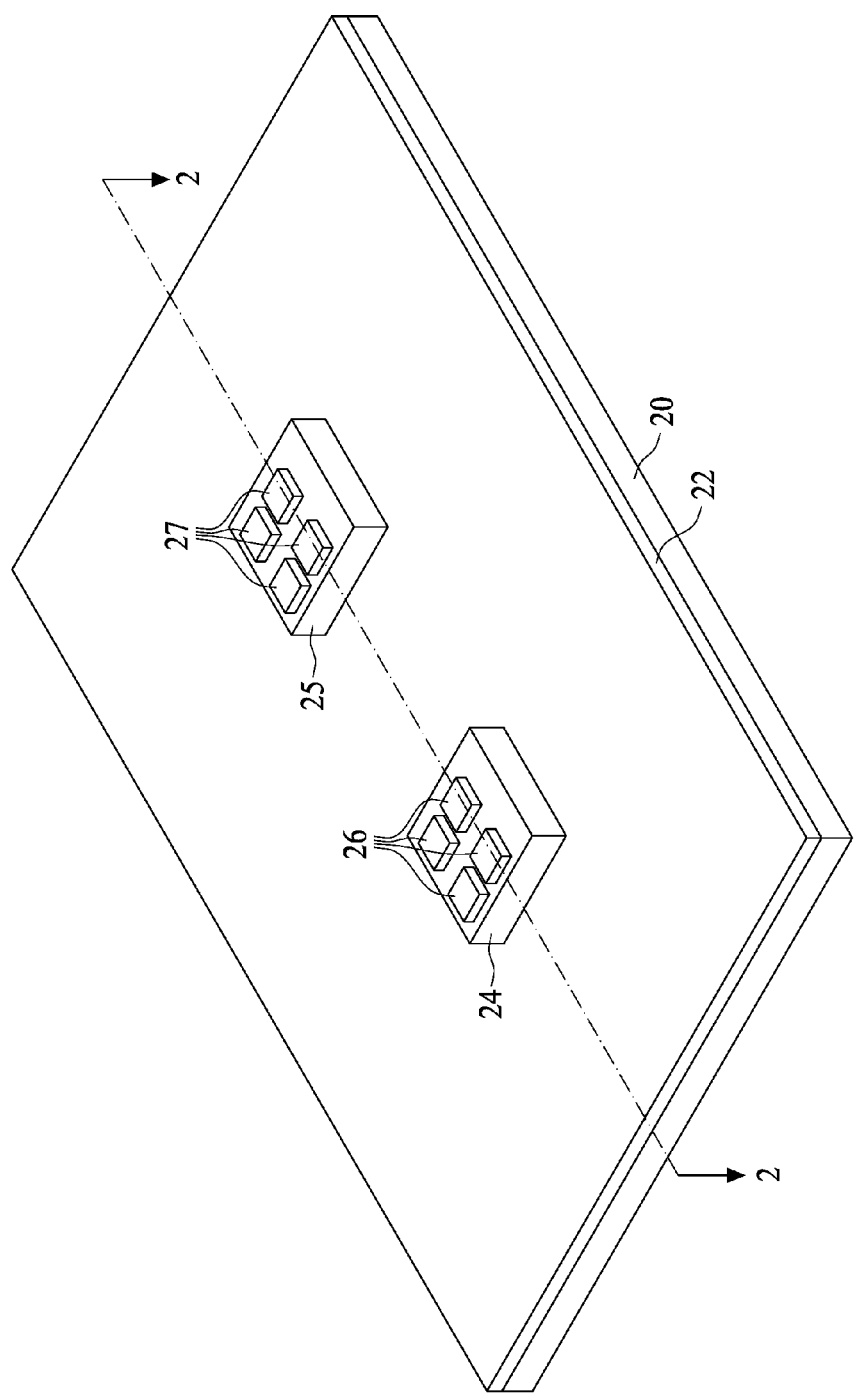

The following disclosure provides many different embodiments, or examples, for implementing different features of the disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

In the present disclosure, an optical sensing system is presented. In an exemplary embodiment, the optical sensing system includes at least a sensor electrically connected to a printed circuit board (PCB), wherein a cavity of the PCB accommodates at least a portion of the sensor, and a secondary optical lens is formed on a material filling and encompassing gaps between the PCB cavity and the sensor. The compact optical sensing system allows for a reduced form factor of final products and provides for cost effective solution applicable to various optical sensing purposes. The intermediate stages of forming the optical sensing system are illustrated. The variations of the embodiments are discussed. Throughout the various views and illustrative embodiments, like reference numbers are used to designate like elements.

FIGS. 1 through 8 are schematic views illustrating intermediate stages in the manufacturing of an optical sensing system in accordance with some exemplary embodiments of the present disclosure. FIG. 1 is a cross-sectional view illustrating a carrier 20, and an adhesive layer 22 on the carrier 20. The carrier 20 may be a glass carrier, a ceramic carrier, or the like. The adhesive layer 22 may be formed of an adhesive such as an adhesive film.

FIG. 2A is a three-dimensional perspective view illustrating the placement of dies 24 and 25 over the carrier 20. The die 24 is placed over the carrier 20 by the side of the die 25. In some embodiments, the dies 24 and 25 are attached to the adhesive layer 22, which is adhered to the carrier 20. The dies 24 and 25 may be a logic device die including logic transistors therein. The die 24 may include power management integrated circuits (PMICs) specifically designed to manage the power consumption of a system. In particular, a PMIC may process the raw voltage from a power supply, such as a battery, and in turn supply regulated voltages to drive a plurality of off-chip power consumption entities separate from the PMIC. A typical PMIC may include many high-power on-chip modules for driving off-chip power consumption entities, such as switched-mode battery chargers (SMBC's), back light display drivers (WLED's), buck regulators, audio amplifiers, and flash LED drivers. The on-chip modules may dissipate considerable power when processing power to or from the off-chip entities. The die 25 may include a microcontroller unit (MCU). The MCU is a computer with a smaller scale on a single integrated circuit containing a processor core, memory, and programmable input/output peripherals.

Electrical connectors 26 and 27 are formed as the top portions of the die 24 and die 25 respectively, and are electrically coupled to the PMICs in the die 24 and the MCU in the die 25. In some embodiments, the electrical connectors 26 and 27 include metal pillars (such as copper pillars), which may be pre-formed before the device die 24 and die 25 are placed over the carrier 20. The metal pillars may be solder-free, and may comprise vertical walls. In some embodiments, dielectric layers are formed at the top surfaces of the die 24 and die 25, with metal pillars having at least lower portions, or entireties, in the dielectric layer. The top surfaces of the dielectric layers may also be substantially level with the top ends of the electrical connectors 26 and 27. The dielectric layers may be comprised of polyimide, polybenzoxazole (PBO), an oxide layer, a nitride layer, or multi-layers thereof. When the dielectric layers are not formed, the metal pillars protrude above the top surfaces of the die 24 and die 25. In this embodiment, the dielectric layers are not depicted in the FIG. 2A and subsequent drawings.

Figure 2B:
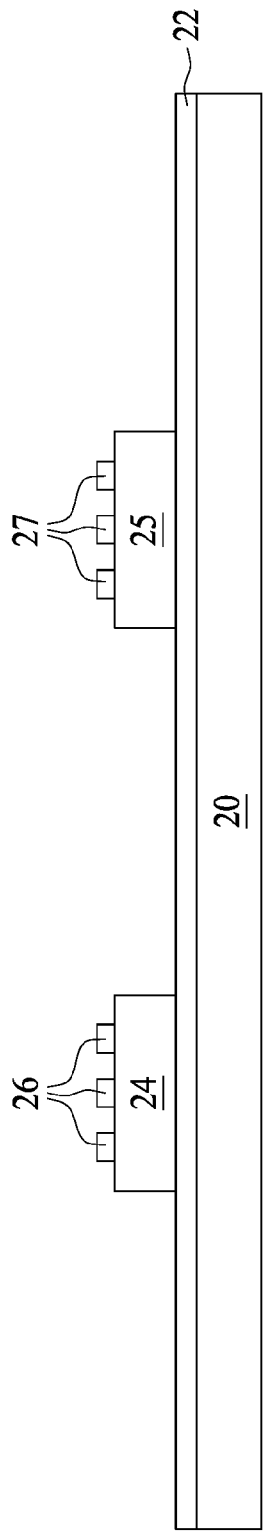

FIG. 2B is a cross-sectional view illustrating the placement of the dies 24 and 25 over the carrier 20 taken along the lines 2-2 of FIG. 2A. The dies 24 and 25 are attached to the adhesive layer 22, which is adhered to the carrier 20. The thicknesses of the dies 24, 25 and the heights of electrical connectors 26 and 27 are controlled so that the top ends of the metal pillars of the dies 24 and 25 are substantially level with each other. Furthermore, since the dies 24 and 25 are placed on the adhesive 22, the back surfaces of the dies 24 and 25 are level with each other.

Figure 2C:
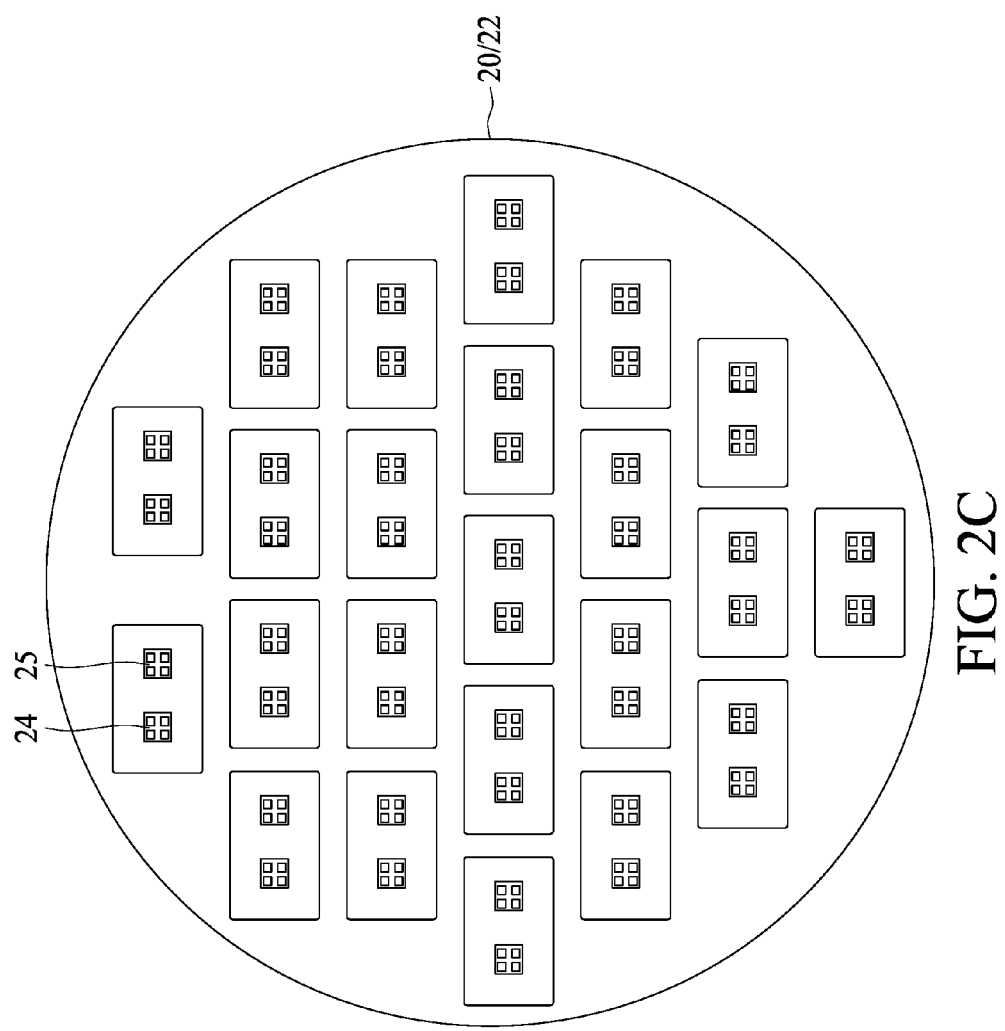

FIG. 2C illustrates a top view of the structure in FIGS. 2A and 2B. In some embodiments, the placement of the dies 24 and 25 is at a wafer level, and hence there are a plurality of dies 24 and 25 placed over the carrier 20. FIG. 2C illustrates that the carrier 20 has a round top-view shape. In alternative embodiments, the carrier 20 may also have a rectangular top-view shape, and the die 24 and die 25 may be laid out as an array. In FIG. 2C, the rectangles (not marked) encircling each groups of the dies 24 and 25 define boundaries of the respective packages formed in subsequent steps.

Figure 3:
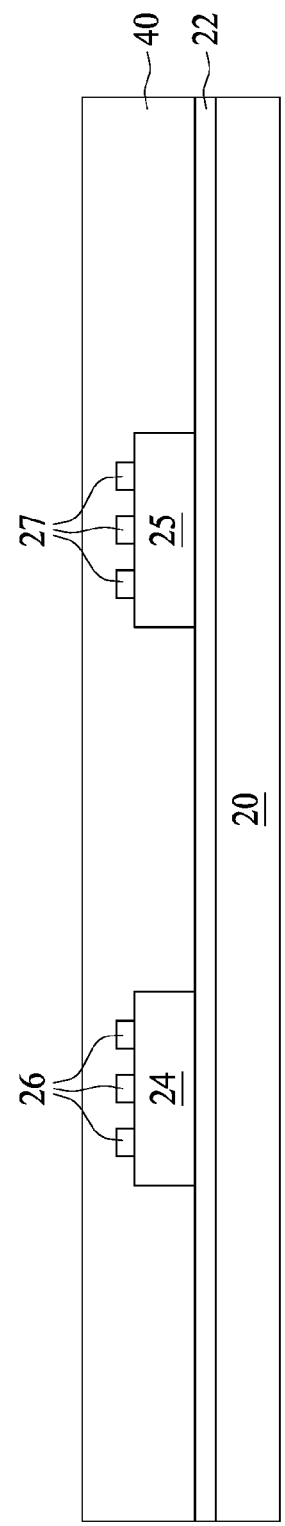

Referring to FIG. 3, a molding material 40 is dispensed and molded on the dies 24 and 25. The molding material 40 fills the gaps between the dies 24 and 25, and may be in contact with the adhesive layer 22. Furthermore, the molding material 40 may be filled into the gaps between the electrical connectors 26 and 27 if the dielectric layers are not formed on the top surface of the dies 24 and 25. The molding material 40 is comprised of a polymer in some embodiments. For example, the molding material 40 may include a molding compound, a molding underfill, an epoxy, or a resin. A top surface of the molding material 40 is higher than the top ends of the electrical connectors 26 and 27. The bottom surface of the molding material 40 is substantially level with the back surfaces of the dies 24 and 25. After being dispensed, the molding material 40 is cured.

Figure 4:
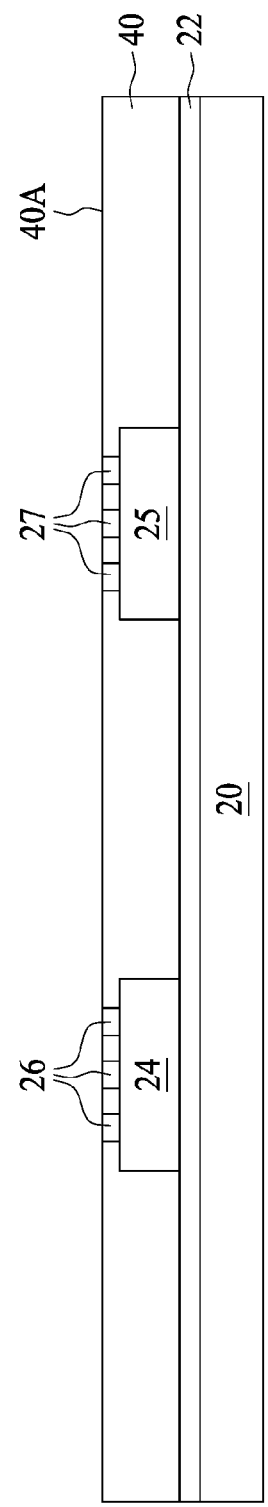

Next, a planarization step, which may be a grinding step or a Chemical Mechanical Polish (CMP) operation, is performed to thin the molding material 40. The planarization step may be completed until the top ends of the electrical connectors 26 and 27 are exposed. The resulting structure is shown in FIG. 4. The top ends of the electrical connectors 26 and 27 in the dies 24 and 25 are level with each other, and are level with a top surface 40A of the molding material 40.

In some embodiments in which no dielectric layer is formed, the molding material 40 encircles, and is in contact with, each of the electrical connectors 26 and 27. In alternative embodiments in which the dielectric layers are formed, the top ends of the electrical connectors 26 and 27 are level with each other, and are substantially level with the surfaces of the dielectric layers and the top surface 40A of the molding material 40.

Figure 5:
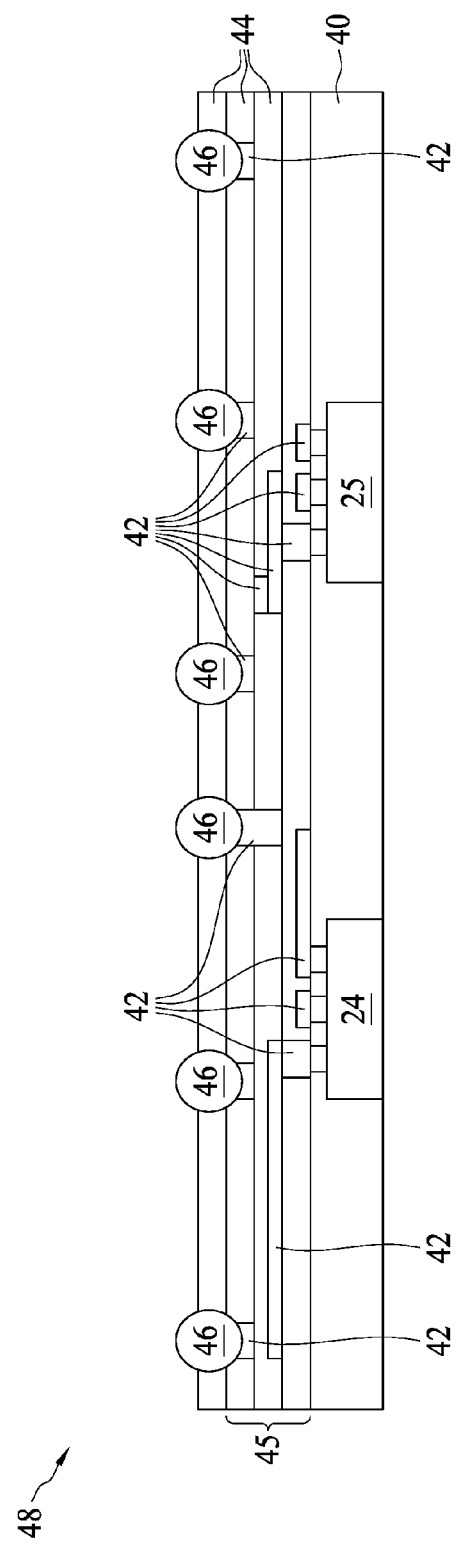

Next, referring to FIG. 5, a redistribution layer (RDL) 45 is formed over the molding material 40. The RDL 45, sometimes also referred to as a re-distribution line, includes dielectric layers 44 and a plurality of connection patterns 42 reside therein. At least a portion of the connection patterns 42 is electrically connected to, and may interconnect, the electrical connectors 26 and 27. There may be one, two, three, or more dielectric layers 44, each including a plurality of connection patterns 42 at the same level. The connection patterns 42 further include vias that interconnect the connection patterns in neighboring redistribution layers. The connection patterns 42 in the bottom redistribution layer and the respective dielectric layer 44 have a bottom surface in contact with the top ends of the electrical connectors 26 and 27 and the top surface 40A of the molding material 40. In some embodiments, the RDL 45 are formed by forming and patterning the dielectric layers 44, and forming the connection patterns 42 in the openings in the patterned dielectric layers 44. In alternative embodiments, the RDL 45 is formed by depositing metal layers, patterning the metal layers, and filling the gaps between the connection patterns 42 with the dielectric layers 44. In yet alternative embodiments, the RDL 45 may be formed using damascene processes. The RDL 45 may be comprised of copper, nickel, palladium, aluminum, tungsten, or the like. The dielectric layers 44 may comprise photo-sensitive materials such as polyimide, PBO, or the like, which may be patterned without using additional photo resists. The dielectric layers 44 may also be formed of a non-organic material or materials such as oxides and/or nitrides.

FIG. 5 also illustrates the formation of electrical connectors 46 in accordance with some exemplary embodiments. The formation of the connectors 46 may include placing solder balls on exposed portions of the connection patterns 42, and reflowing the solder balls. In alternative embodiments, the formation of the connectors 46 includes performing a plating step to form copper or solder regions over the exposed portions of the connection patterns 42. The connectors 46 may also include metal pillars, or metal pillars and solder caps, which may also be formed through plating. In some embodiments, the combined structure including the dies 24, 25, the molding material 40, the overlying RDL 45 and the connectors 46 is referred to as an Integrated Fan Out (InFO) assembly or a fan-out package 48. The carrier 20 is detached from the package 48 and the adhesive layer 22 may be removed in the subsequent operations. The fan-out package 48 occupies a portion of a wafer that includes a plurality of fan-out packages, and the wafer is die-sawed along scribe lines into a plurality of fan-out packages.

Figure 6:
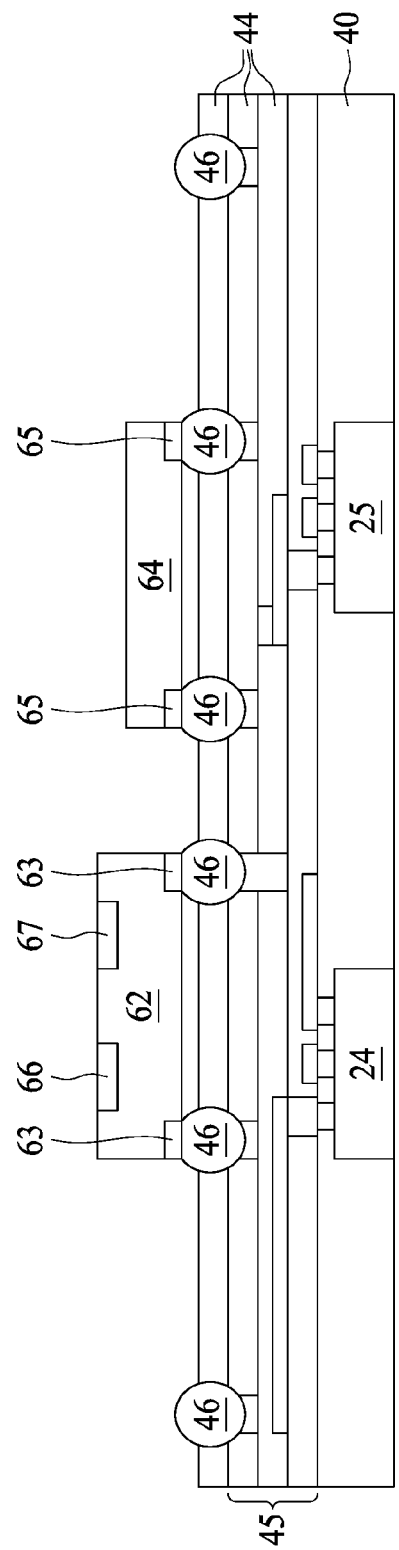

FIG. 6 is a cross-sectional view illustrating the placement of sensors 62 and 64 over the fan-out package 48 in accordance with some exemplary embodiments. In this embodiment, the sensor 62 may be a measuring device designed for measuring heart rate, i.e. an optical heart rate sensor. The optical heart rate sensor 62, for example, is employed to improve physical and mental condition efficiently and safely. The user can employ an optical heart rate sensor 62 to monitor his heart rate level during exercising, for example, and avoid excessive stress. An optical heart rate sensor can also be utilized in slimming since it has been scientifically shown that the most efficient way to burn fat stored in the body is to exercise at a given heart rate (about 55 to 65%) of a person's maximum heart rate. An example optical heart rate sensor has more than one light emitting diode that provides light source projected to skin through a lens element 66. An optical detector mounted close to the light source can detect the movement of blood under the skin of the wrist based on light reflected from the skin. The optical detector can detects blood movement by receiving a portion of the emitting light through a lens element 67. The portion of the emitting light can be the initial light emitted by the light emitting diodes subtracted by an amount absorbed by skin. The lens elements 66 and 67 may be referred to as the first or primary optic as well.

The sensor 64 may be a motion sensor for correcting artifacts sensed by the optical heart rate sensor 62 due to user's motion. The motion sensor 64 may be a MEMS-based multi-dimensional accelerometer. For example, the motion sensor 64 may be a three dimensional accelerometer composed of three accelerometers disposed along ee orthogonal measurement axis and providing three dimensional acceleration data representative of the acceleration to which the device is subjected. The optical heart rate sensor 62 and motion sensor 64 may be bonded to fan-out package 48 by electrically connecting bond pads 63 and 65 to the electrical connectors 46.

Figure 7:
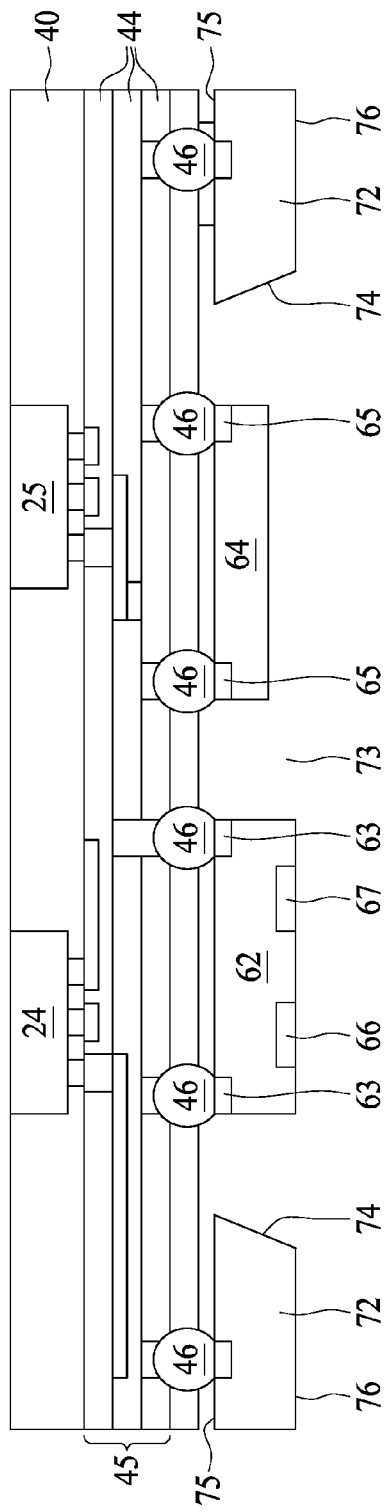

FIG. 7 is a cross-sectional view illustrating the bonding of fan-out package 48 onto a PCB 72 in accordance with some exemplary embodiments. As shown in FIG. 7, the fan-out package 48 with the optical heart rate sensor 62 and motion sensor 64 bonded thereto is directly mounted onto a PCB 72 using a flip-chip technique through the electrical connectors 46. The PCB 72 includes a continuous cavity 73 defined by a sidewall 74 of the PCB 72. The continuous cavity 73 provides a space for accommodating the optical heart rate sensor 62 and motion sensor 64 bonded to the fan-out package 48. In this embodiment, the continuous cavity 73 is a through cavity, which extends downwardly from a top surface 75 to a bottom surface 76 of the PCB 72 as shown in FIG. 7.

A dimension of the through cavity 73 may be determined according to a dimension of the optical heart rate sensor 62 and motion sensor 64 that extends into the through cavity 73 of the PCB 72. As a consequence, the entire optical sensing system including the fan-out package 48, the optical heart rate sensor 62, the motion sensor 64 and the PCB 72 can have a compact form factor which is thinner. When the optical sensing system is integrated into a device, such as a wrist watch including a heart rate measurement function, the thinner optical sensing system allow for a reduced thickness of the wrist watch. In addition, a distance between user's skin and the primary optic of the optical heart rate sensor 62 may be incidentally reduced through the optical sensing system shown in FIG. 7, thereby improving the accuracy and sensitivity of the optical sensing system. In order to receive more light reflected from user's skin, the sidewall 74 of cavity 73 of the PCB 72 may be intentionally tilted toward the bottom surface 76. However, this is not a limitation of the present disclosure. In some embodiments, the sidewall 74 of cavity 73 of the PCB 72 may be perpendicular to the top surface 75 and the bottom surface 76.

Figure 8:
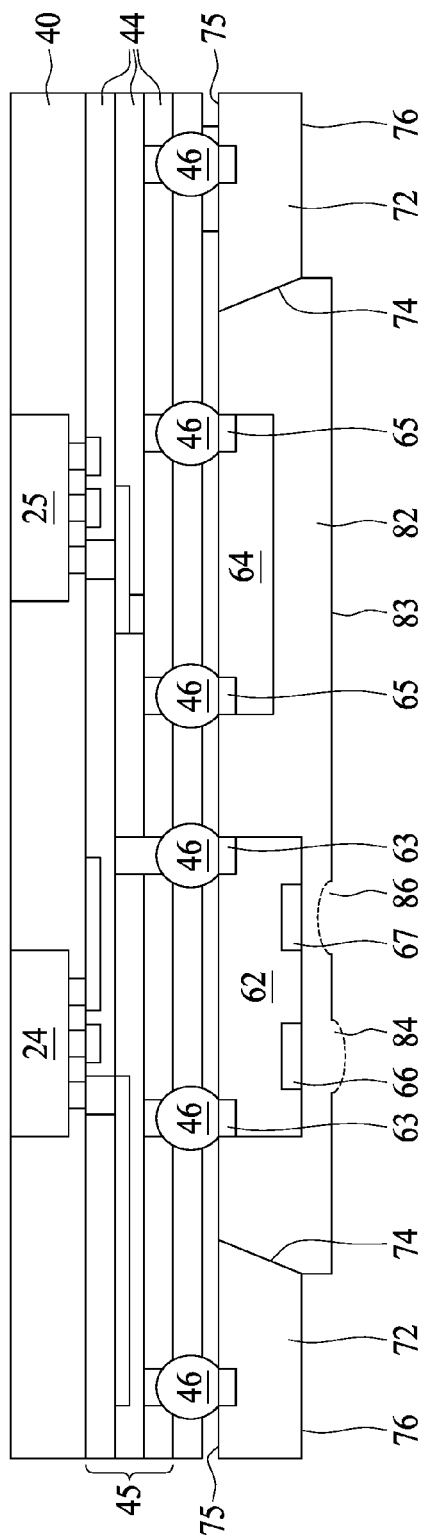

In order to further enhance performance of the optical sensing system, a secondary optic structure may be employed. FIG. 8 is a cross-sectional view illustrating the forming of a secondary optic 82 onto the primary optic of the optical heart rate sensor 62 in accordance with some exemplary embodiments. In accordance with the present disclosure, different categories or types of secondary optics 82 may be used to apply optical properties of the underlying construction material and incorporate different specialized geometries that turn the primary optic of the optical heart rate sensor 62 into a more useful one. The secondary optics 82 includes a convex structure 84 protruding from a bottom surface 83 of the secondary optics 82. When the light is emitted from the light source, the concave structure 86 can receive the light reflected from the skin. A central point of the convex structure 84 is located at a pathway that a perpendicular light emitted from the light source behind the lens element 66 passes through in order to more evenly distribute emitted light on user's skin. The secondary optics 82 further includes a concave structure 86 recessed into the bottom surface 83 of the secondary optics 82. A central point of the concave structure 86 is located at a pathway that a perpendicular light reflected from the skin passes through in order to increase total amount of incident light for the lens element 67.

The convex structure 84 and concave structure 86 may be formed on a material filling and encompassing gaps between the PCB cavity 73 and the optical heart rate sensor 62 and the motion sensor 64 as shown in FIG. 8. The material may be comprised of any polymers including Polycarbonate (PC), Polyethylene terephthalate Resin (PET) and Polymethylmethacrylate (PMMA), and glass. Moreover, the bottom surface 83, the convex structure 84 and the concave structure 86 can be fabricated by using single molding process to simplify manufacturing process and save cost. In some embodiments, a distance between the primary optics and the secondary optics, or for example, a distance between a light emitting diode and the convex lens is designed to be about 500 micrometer in order to retain the compactness of the package.

Figure 9:
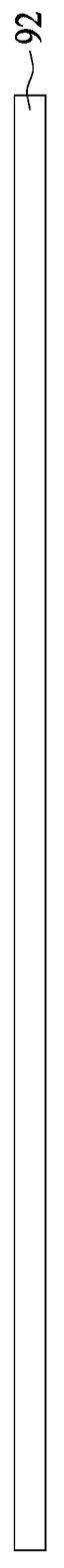

In some embodiments, the concept of the present disclosure may be reflected in an optical sensing system having a more generic structure. FIGS. 9 through 13 are schematic views illustrating intermediate stages in the manufacturing of an optical sensing system in accordance with some exemplary embodiments of the present disclosure. FIG. 9 is a cross-sectional view illustrating a PCB 92. The PCB 92 shown in FIG. 9 is similar to that in FIG. 8.

Figure 10:
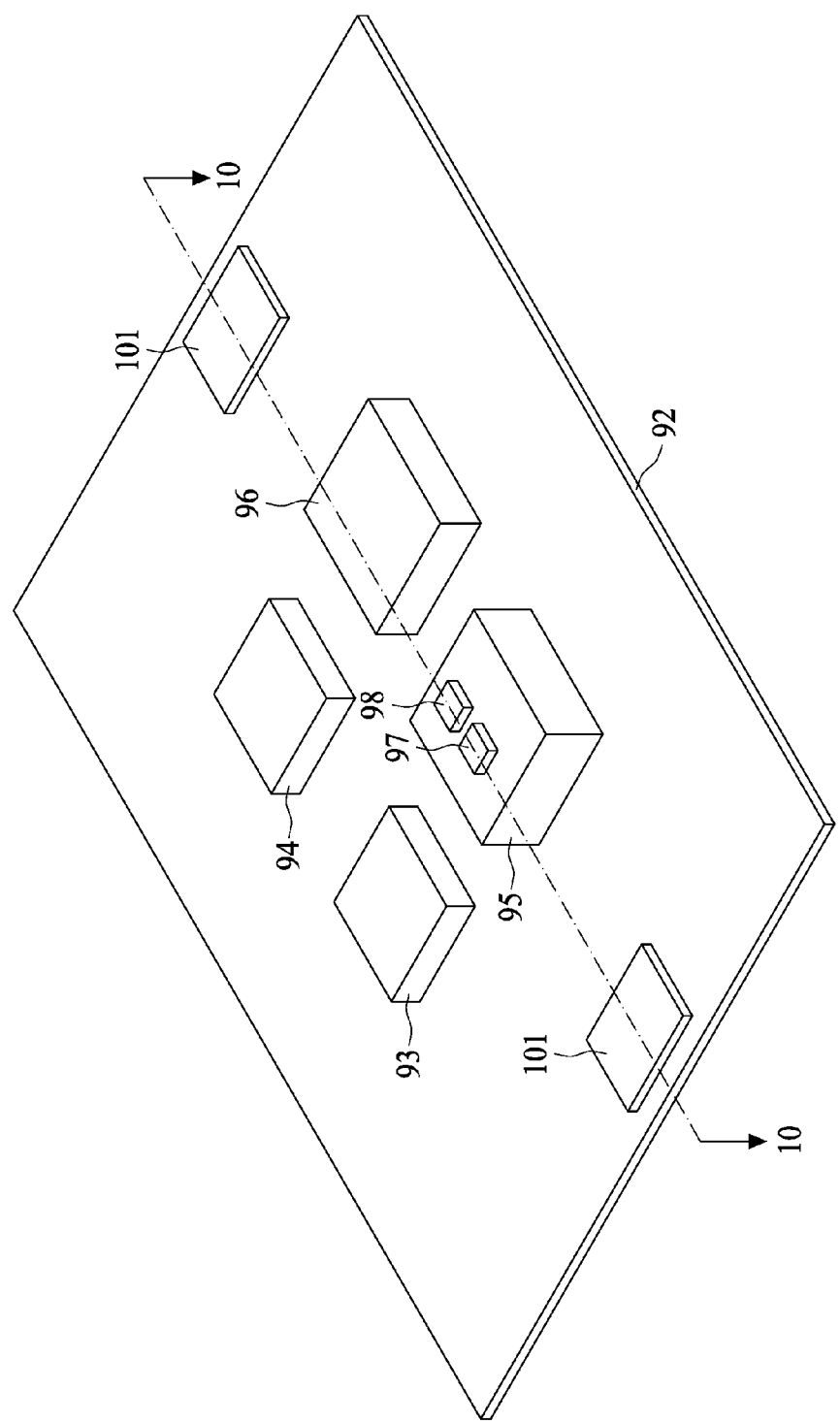

FIG. 10 is a three-dimensional perspective view illustrating the placement of dies 93-96 over the PCB 92. The dies 93-96 may be placed over the PCB 92 side by side as shown in FIG. 10. In some embodiments, the dies 93-96 may be placed over the PCB 92 in other arrangements. The dies 93-96 may be bonded and electrically connected to the PCB 92 through bonding pads. In some embodiments, the PCB 92 may be replaced by any other types of carrier including conductive patterns therein. The dies 93 and 94 may be a logic device die including logic transistors therein. The die 93 may include power management integrated circuits (PMICs) specifically designed to manage the power consumption of a system. In particular, a PMIC may process the raw voltage from a power supply, such as a battery, and in turn supply regulated voltages to drive a plurality of off-chip power consumption entities separate from the PMIC. A typical PMIC may include many high-power on-chip modules for driving off-chip power consumption entities, such as switched-mode battery chargers (SMBC's), back light display drivers (WLED's), buck regulators, audio amplifiers, and flash LED drivers. The on-chip modules may dissipate considerable power when processing power to or from the off-chip entities. The die 94 may include a microcontroller unit (MCU). The MCU is a computer with a smaller scale on a single integrated circuit containing a processor core, memory, and programmable input/output peripherals.

The die 95 may be a measuring device designed for measuring heart rate, i.e. an optical heart rate sensor. The optical heart rate sensor 95, for example, is employed to improve physical and mental condition efficiently and safely. The user can employ an optical heart rate sensor 95 to monitor his heart rate level during exercising, for example, and avoid excessive stress. An optical heart rate sensor can also be utilized in slimming since it has been scientifically shown that the most efficient way to burn fat stored in the body is to exercise at a given heart rate (about 55 to 65%) of a person's maximum heart rate. An example optical heart rate sensor has two light emitting diodes that provide light source projected to skin through a lens element 97. An optical detector mounted close to the light source can detect the movement of blood under the skin of the wrist based on light reflected from the skin. The optical detector can detects blood movement by emitting light onto skin and measuring the amount of light absorbed by skin through a lens element 98. The lens elements 97 and 98 may be referred to as the first or primary optic as well.

Figure 11:
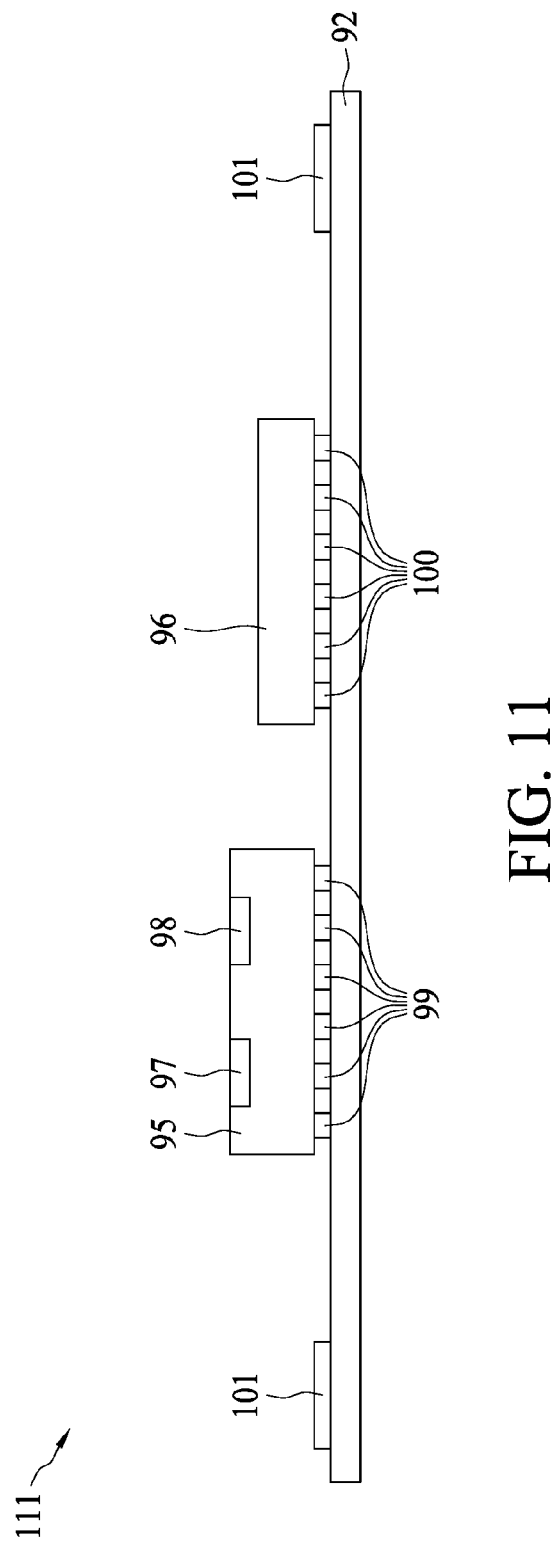

The sensor 96 may be a motion sensor for correcting artifacts sensed by the optical heart rate sensor 95 due to user's motion. The motion sensor 96 may be a MEMS-based multi-dimensional accelerometer. For example, the motion sensor 96 may be a three dimensional accelerometer composed of three accelerometers disposed along three orthogonal measurement axis and providing three dimensional acceleration data representative of the acceleration to which the device is subjected. In FIG. 11, the optical heart rate sensor 95 and motion sensor 96 may be bonded to the PCB 92 by electrically connecting bond pads 99 and 100 to conductive connectors the PCB 92 and forms a PCB bridge 111.

Figure 12:
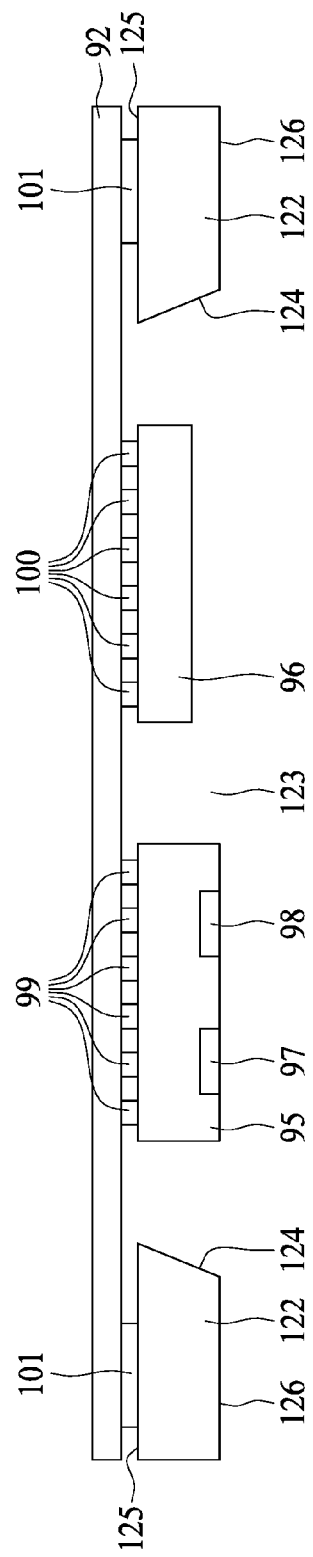

FIG. 12 is a cross-sectional view illustrating the bonding of the PCB bridge 111 onto a PCB 122 in accordance with some exemplary embodiments. As shown in FIG. 12, the flipped PCB bridge 111 with the optical heart rate sensor 95 and motion sensor 96 bonded thereto is directly mounted onto a PCB 122 through electrical connectors 101. The PCB 122 includes a continuous cavity 123 defined by a sidewall 124 of the PCB 122. The continuous cavity 123 provides a space for accommodating the optical heart rate sensor 95 and motion sensor 96 bonded to the PCB 92. In this embodiment, the continuous cavity 123 is a through cavity, which extends downwardly from a top surface 125 to a bottom surface 126 of the PCB 122 as shown in FIG. 12.

A dimension of the through cavity 123 may be determined according to a dimension of the optical heart rate sensor 95 and motion sensor 96 that extends into the through cavity 123 of the PCB 122. As shown in FIG. 12, the optical heart rate sensor 95 possesses a thickness greater than that of the motion sensor 96 and the dies 93, 94 (see FIG. 10), and thus the dimension of the through cavity 123 (i.e., a distance between the top surface 125 and a bottom surface 126 of the PCB 122) is determined by the thickness-limiting element, i.e., the heart rate sensor 95. In some embodiments, the dimension of the through cavity 123 can be from about 1 mm to about 1.2 mm. As a consequence, the entire optical sensing system including the PCB bridge 111 and the PCB 122 can have a compact form factor which is thinner. When the optical sensing system is integrated into a device, such as a wrist watch including a heart rate measurement function, the thinner optical sensing system allow for a reduced thickness of the wrist watch. In addition, a distance between user's skin and the primary optic of the optical heart rate sensor 95 may be incidentally reduced through the optical sensing system shown in FIG. 12, thereby improving the accuracy and sensitivity of the optical sensing system. In order to receive more light reflected from user's skin, the sidewall 124 of cavity 123 of the PCB 122 may be intentionally tilted toward the bottom surface 126. However, this is not a limitation of the present disclosure. In some embodiments, the sidewall 124 of cavity 123 of the PCB 122 may be perpendicular to the top surface 125 and the bottom surface 126.

Figure 13:
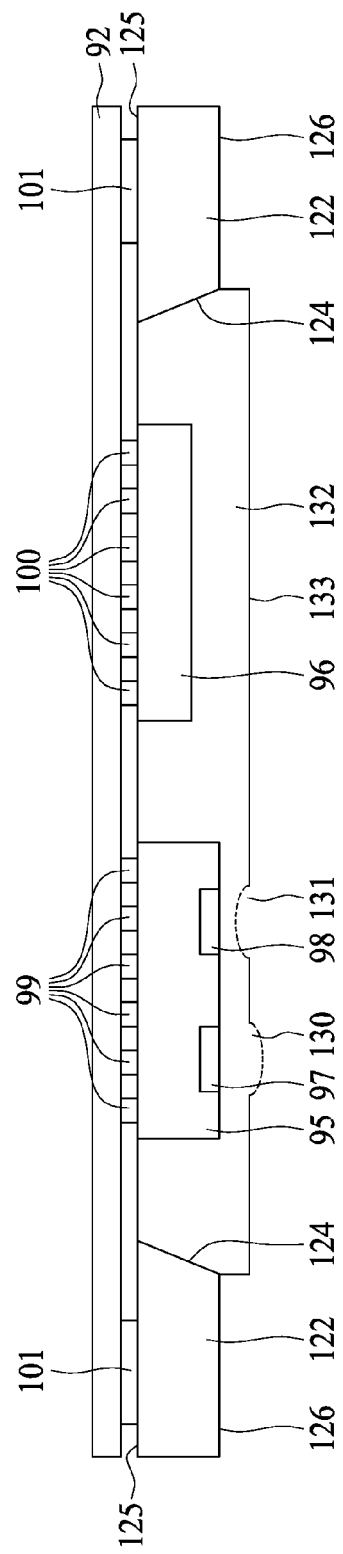

In order to further enhance performance of the optical sensing system, a secondary optic structure may be employed. FIG. 13 is a cross-sectional view illustrating the forming of a secondary optic 132 onto the primary optic of the optical heart rate sensor 95 in accordance with some exemplary embodiments. In accordance with the present disclosure, different categories or types of secondary optics 132 may be used to apply optical properties of the underlying construction material and incorporate different specialized geometries that turn the primary optic of the optical heart rate sensor 95 into a more useful one. The secondary optics 132 includes a convex structure 130 protruding from a bottom surface 133 of the secondary optics 132. A central point of the convex structure 130 is located at a pathway that a perpendicular light emitted from the light source behind the lens element 97 passes through in order to more evenly distribute emitted light on user's skin. The secondary optics 132 further includes a concave structure 131 recessed into the bottom surface 133 of the secondary optics 132. When the light is emitted from the light source, the concave structure 131 can receive the light reflected from the skin. A central point of the concave structure 131 is located at a pathway that a perpendicular light reflected from the skin passes through in order to increase total amount of incident light for the lens element 98.

The convex structure 130 and concave structure 131 may be formed on a material filling and encompassing gaps between the PCB cavity 123 and the optical heart rate sensor 95 and the motion sensor 96 as shown in FIG. 12. The material may be comprised of any polymers including Polycarbonate (PC), Polyethylene terephthalate Resin (PET) and Polymethylmethacrylate (PMMA), and glass. Moreover, the bottom surface 133, the convex structure 130 and the concave structure 131 can be fabricated by using single molding process to simplify manufacturing process and save cost.

Figure 14:
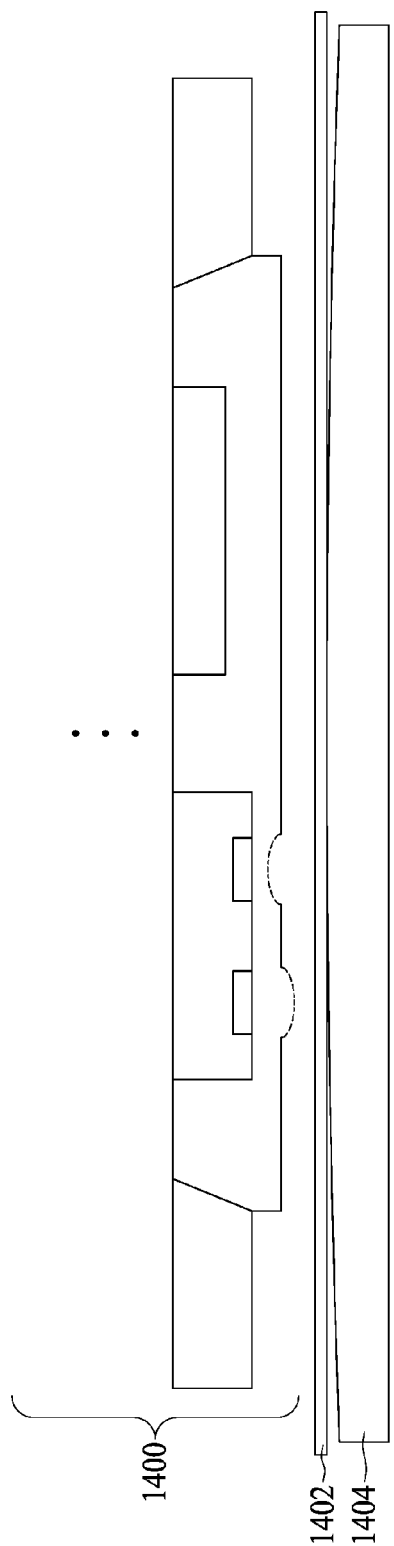
FIG. 14 is a cross-sectional view illustrating the integration of an optical sensing system into an electronic device in accordance with some exemplary embodiments.

FIG. 14 is a cross-sectional view illustrating the integration of an optical sensing system into an electronic device in accordance with some exemplary embodiments. An optical sensing system 1400 may be the optical sensing system shown in FIG. 7, 8, 12 or 13. The optical sensing system 1400 may be integrated into an electronic device, such as an electronic wrist watch or a heart rate monitor. The electronic device includes a housing, and a flat glass 1402 is located at a bottom surface of the housing. When a user wears the electronic device, the flat glass 1402 of the electronic device contacts with skin of the user 1404 so that the optical sensing system 1400 can obtain a sensing result through the flat glass 1402. Since the secondary optic structure is embedded in the optical sensing system 1400, the bottom surface of the electronic device can be simple and thin without too much further process on it. Please note that the flat glass 1402 may be replaced by any other flat transparent materials. For example, in some embodiments, the transparent material may be a flat sapphire glass.

Some embodiments of the present disclosure provide an optical sensing system, including: a printed circuit board (PCB) including a top surface, a bottom surface and a through cavity, wherein the through cavity extends downwardly from the top surface to the bottom surface; a supporter having a top surface and a bottom surface; and an optical sensor bonded and coupled to the top surface of the supporter, wherein the optical sensor includes a primary optic structure; wherein the supporter is flipped over and bonded to the PCB with the top surface facing the through cavity, so that the optical sensor is coupled to the PCB and at least partially extends to the through cavity.

In some embodiments of the present disclosure, the optical sensing system further includes a secondary optic structure at least disposed over the primary optic structure of the optical sensor.

In some embodiments of the present disclosure, the secondary optic structure includes a convex structure located at a pathway that a perpendicular light emitted from a light source behind the primary optic structure passes through.

In some embodiments of the present disclosure, the secondary optic structure further includes a concave structure, and when light is emitted from the light source and bounces off an object, the concave structure receives light reflected from the object.

In some embodiments of the present disclosure, the secondary optic structure further fills and encompasses gaps between the through cavity and the optical sensor.

In some embodiments of the present disclosure, the optical sensor is a heart rate sensor.

In some embodiments of the present disclosure, the optical sensing system further includes a motion sensor bonded and coupled to the top surface of the supporter, and the motion sensor is at least partially extends to the through cavity.

In some embodiments of the present disclosure, the optical sensing system further includes a die bonded and coupled to the supporter, wherein the die includes a power management integrated circuits (PMICs) or a microcontroller unit (MCU).

In some embodiments of the present disclosure, the die is bonded and coupled to the top surface of the supporter.

In some embodiments of the present disclosure, a sidewall of the through cavity is tilted toward the bottom surface of the PCB.

Some embodiments of the present disclosure provide an optical sensing system, including: a printed circuit board (PCB) including a top surface, a bottom surface and a through cavity, wherein the through cavity extends downwardly from the top surface to the bottom surface; a chip package including a top surface and a bottom surface, wherein a plurality of electrical connectors is located at the bottom surface of the chip package; and an heart rate sensor bonded and coupled to the bottom surface of the chip package, wherein the heart rate sensor includes a primary optic structure, a light source and a photo diode; wherein the chip package is bonded to the PCB through the electrical connectors and with the bottom surface facing the through cavity, so that the heart rate sensor is coupled to the PCB and at least partially extends to the through cavity.

In some embodiments of the present disclosure, the optical sensing system further includes a secondary optic structure at least disposed over the primary optic structure of the heart rate sensor, wherein the secondary optic structure includes a convex structure and a concave structure.

In some embodiments of the present disclosure, the secondary optic structure further fills and encompasses gaps between the through cavity and the heart rate sensor.

In some embodiments of the present disclosure, the chip package is a fan-out package and includes a power management integrated circuit (PMIC) die and a microcontroller unit (MCU) die.

In some embodiments of the present disclosure, a sidewall of the through cavity is tilted toward the bottom surface of the PCB.

Some embodiments of the present disclosure provide an electronic device, including: a housing, including a flat transparent material at a bottom surface of the housing; and an optical sensing system of claim 1 disposed in the housing; wherein the optical sensor senses an object around the electronic device through the flat transparent material.

In some embodiments of the present disclosure, the flat transparent material is a flat glass.

In some embodiments of the present disclosure, the flat transparent material is a flat sapphire glass.

In some embodiments of the present disclosure, the electronic device is an electronic wrist watch or a heart rate monitor.

Some embodiments of the present disclosure provide an electronic device, including: a housing, including a flat transparent material at a bottom surface of the housing; and an optical sensing system of claim 11 disposed in the housing; wherein the optical sensor senses an object around the electronic device through the flat transparent material.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An optical sensing system, comprising:
a printed circuit board (PCB) comprising a top surface and a bottom surface;
a supporter having a first surface and a second surface opposite to the first surface;
an optic structure extending downwardly from the top surface through the bottom surface of the PCB; and
a sensor bonded and electrically coupled to the first surface of the supporter, the sensor including a light source, an optical detector, a first lens element and a second lens element, the light source being between the first lens element and the supporter, and the optical detector being between the second lens element and the supporter, wherein a width of the optic structure is greater than a width of the sensor;
wherein the supporter is bonded to the PCB with the first surface of the supporter facing the optic structure, so that the sensor and the PCB are at the same side of the supporter, the sensor is electrically coupled to the PCB through the supporter, and the sensor at least partially extends to the optic structure.

2. The optical sensing system of claim 1, wherein the optic structure at least covering the first lens element and the second lens element of the sensor.

3. The optical sensing system of claim 2, wherein the optic structure comprises a convex structure covering the first lens element, and the first lens element is between the convex structure and the light source.

4. The optical sensing system of claim 3, wherein the optic structure further comprises a concave structure covering the second lens element, and the second lens element is between the concave structure and the optical detector.

5. The optical sensing system of claim 2, wherein the optic structure further fills and encompasses spaces between the substrate and the optical sensor.

6. The optical sensing system of claim 1, wherein the optical sensor is a heart rate sensor.

7. The optical sensing system of claim 1, further comprising a motion sensor bonded and coupled to the first surface of the supporter, and the motion sensor is at least partially extends to the optic structure.

8. The optical sensing system of claim 1, further comprising a die bonded and coupled to the supporter, wherein the die comprises a power management integrated circuits (PMICs) or a microcontroller unit (MCU).

9. The optical sensing system of claim 8, wherein the die is bonded and coupled to the second surface of the supporter.

10. The optical sensing system of claim 1, wherein a sidewall of the optic structure is tilted toward the bottom surface of the PCB.

11. An electronic device, comprising:
a housing, comprising a flat transparent material at a bottom surface of the housing; and
an optical sensing system disposed in the housing, the optical sensing system comprising:
a printed circuit board (PCB) comprising a top surface and a bottom surface;
a supporter having a first surface and a second surface opposite to the first surface;
an optic structure extending downwardly from the top surface through the bottom surface of the PCB; and
a sensor bonded and electrically coupled to the first surface of the supporter, the sensor including a light source, an optical detector, wherein a width of the optic structure is greater than a width of the sensor;
wherein the supporter is bonded to the PCB with the first surface of the supporter facing the optic structure, so that the sensor and the PCB are at the same side of the supporter, the sensor is electrically coupled to the PCB through the supporter, and the sensor at least partially extends to the optic structure;
wherein the sensor senses an object around the electronic device through the flat transparent material.

12. The electronic device of claim 11, wherein the flat transparent material is a flat glass.

13. The electronic device of claim 11, wherein the flat transparent material is a flat sapphire glass.

14. The electronic device of claim 11, wherein the electronic device is an electronic wrist watch or a heart rate monitor.

15. An optical sensing system, comprising:
a substrate comprising a top surface and a bottom surface;
a chip package including a die, a redistribution layer (RDL) and a plurality of electrical connectors, the RDL being between the die and the electrical connectors;
an optical sensor bonded and electrically coupled to the electrical connectors, wherein the optical sensor comprises a primary optic structure; and
a secondary optic structure extending downwardly from the top surface through the bottom surface of the PCB, wherein a width of the secondary optic structure is greater than a width of the optical sensor;
wherein the chip package is bonded to the substrate through the electrical connectors, so that the optical sensor is electrically coupled to the substrate and the die and at least partially in the secondary optic structure.

16. The optical sensing system of claim 15, wherein the secondary optic structure at least covering the primary optic structure of the optical sensor.

17. The optical sensing system of claim 16, wherein the secondary optic structure comprises a convex structure.

18. The optical sensing system of claim 17, wherein the secondary optic structure further comprises a concave structure.

19. The optical sensing system of claim 16, wherein the secondary optic structure further fills and encompasses spaces between the substrate and the optical sensor.

20. The optical sensing system of claim 15, wherein the optical sensor is a heart rate sensor.

* * * * *